(12) United States Patent
Crain

(10) Patent No.: US 8,075,927 B1
(45) Date of Patent: Dec. 13, 2011

(54) PET REPELLANT TIRE DRESSING

(76) Inventor: Gary Alton Crain, Canton, MS (US)

( * ) Notice: Subject to any disclaimer, the term of this patent is extended or adjusted under 35 U.S.C. 154(b) by 538 days.

(21) Appl. No.: 12/175,759

(22) Filed: Jul. 18, 2008

Related U.S. Application Data

(60) Provisional application No. 60/951,987, filed on Jul. 26, 2007.

(51) Int. Cl.
*A61K 36/05* (2006.01)
*A61K 36/81* (2006.01)
*A61K 36/00* (2006.01)

(52) U.S. Cl. .................. 424/739; 424/760; 424/725

(58) Field of Classification Search .................. None
See application file for complete search history.

(56) References Cited

U.S. PATENT DOCUMENTS

| | | | |
|---|---|---|---|
| 3,923,997 A | 12/1975 | Meuly | |
| 4,455,304 A | 6/1984 | Yaralian | |
| 4,853,413 A | 8/1989 | Katz et al. | |
| 5,364,626 A | 11/1994 | Hasegawa et al. | |
| 5,741,553 A | 4/1998 | Manolas et al. | |
| 2001/0041694 A1 | 11/2001 | Clark et al. | |
| 2003/0060379 A1* | 3/2003 | Souter et al. | 510/131 |
| 2006/0057172 A1 | 3/2006 | Anderson et al. | |
| 2006/0257443 A1 | 11/2006 | Johal | |
| 2008/0050409 A1* | 2/2008 | Pechko et al. | 424/405 |

OTHER PUBLICATIONS

DW ACC 2005-767974, Nov. 2005, Derwent, Fried et al.*
DW ACC 1978-32608A, Mar. 1978, Derwent, Okada.*
DW ACC 2003-568928, May 2003, Derwent, Bleckmann et al.*

* cited by examiner

*Primary Examiner* — Christopher R Tate
*Assistant Examiner* — Randall Winston

(57) ABSTRACT

The present invention discloses a non-toxic, long-lasting tire dressing with pet repellent qualities which enhances the appearance of a vehicle's tires while deterring animals from urinating on the tires. The present invention relates to a new pet repellent tire dressing includes silicone, a solvent, citronella oil, cinnamon oil, and piper nigrum oil. In one embodiment, the citronella oil ranges from about 0.1% to 4% by weight, the cinnamon oil ranges from about 0.04% to 1.6% of the solution by weight, the piper nigrum oil ranges from about 0.01% to 0.4% of the solution, by weight, a solvent and silicone. In one embodiment, the pet repellent tire dressing also includes a dye up to the amount of 0.02% by weight.

20 Claims, No Drawings

PET REPELLANT TIRE DRESSING

CROSS-REFERENCE TO RELATED APPLICATIONS

This application claims priority of U.S. Patent Application Ser. No. 60/951,987 filed on Jul. 26, 2007, which is hereby incorporated by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

The present invention relates to tire care chemicals and pet repellents. More specifically, the present invention relates an improved tire dressing which gives tires a glossy, like-new appearance and has pet repellent qualities.

Many animals, particularly male dogs, tend to urinate on vehicle tires in order to mark their territory and to override the scent of other animals. When dogs urinate on the vehicle's tires, the tires loose their shiny finish and take on a dull and worn appearance. Even when a tire dressing has been applied to give the tire a glossy, like-new look, animal urine still gives the tire a worn and dull appearance. The tire dressing may be washed off the tire surface by the urine.

This dull and worn appearance is undesirable, particularly to vehicle owners who are interested in maintaining a clean, like-new appearance of their car. And no vehicle owner wants to expend time and effort washing and detailing his car including shining his tires, only to have his efforts negated by man's best friend.

None of the commercially available tire dressings have pet repellent qualities. There are pet deterrent products which are commercially available such as oils and sprays, but these products evaporate quickly and are easily washed away by weather and driving conditions. These products are difficult to apply to a tire and often do not spread evenly on the surface of the tire. Additionally, when these products are applied to a tire, they give the tire an unappealing, dull appearance.

One object of the present invention is to provide a high quality, pet repellent tire dressing that shines tires to a glossy, like-new appearance while discouraging animals from urinating on the tires. Another object of the present invention is to provide a high quality, pet repellent tire dressing which is long-lasting. Another object of the present invention is to provide a high quality, pet repellent tire dressing which is non-toxic and safe to use with animals. Another objective of the present invention is to provide a high quality, pet repellent tire dressing that is effective, marketable, and cost effective.

BRIEF SUMMARY OF THE INVENTION

The present invention discloses a non-toxic, long-lasting tire dressing with pet repellent qualities which enhances the appearance of a vehicle's tires while deterring animals from urinating on the tires. The present invention relates to a new pet repellent tire dressing comprising silicone, a solvent, citronella oil, cinnamon oil, and piper nigrum oil. In one embodiment, the citronella oil ranges from 0.1% to 4.0% by weight of the solution. The cinnamon oil ranges from 0.04% to 1.6% of the solution by weight. The piper nigrum oil ranges from 0.01% to 0.4% of the solution by weight. The remainder is silicone and a solvent.

DETAILED DESCRIPTION OF THE INVENTION

The present invention relates to a new pet repellent tire dressing comprising silicone, a solvent, citronella oil, cinnamon oil, and piper nigrum oil. The present invention is non-toxic and long-lastingtire dressing. The pet repellant tire dressing of the present invention has a stable shelf-life of over one year. The present invention enhances the appearance of a vehicle's tires, repels animals away from surfaces where it is applied, and deters animals from urinating on surfaces where it is applied. The present invention is easily sprayed or rubbed on surfaces such as tires and coats these surfaces in a consistent, even manner. Another benefit of the present invention is that it alleviates the corrosive effect that pet urine has on the surface of a vehicle's wheels, hub caps, etc.

Several different commercially available tire dressings were tested for pet repellent effectiveness by applying each dressing to a vehicle tire and walking several different dogs past the treated tires. The commercially available tire dressings had no pet repellent properties. When commercially available pet repellent chemicals are sprayed on tires, the tires have a dull, unappealing, splotchy appearance. Moreover, these chemicals are easily removed from tires when the vehicle is driven or exposed to inclement weather such as a rain or snow shower.

None of the pet repellant oils accomplished the dual purposes of shining vehicle tires and repelling pets from the tires. It is known that organic molecules, such as these pet repellant oils, deteriorate over time when exposed to light, water and other environmental conditions. It was unknown whether the pet repellant oils would combine with silicone to create a homogenous solution that accomplishes the dual purpose of shining vehicle tires and repelling pets from the tires. The pet repellant tire dressing of the present invention encapsulates the citronella oil, cinnamon oil, and piper nigrum oil in the silicone thus protecting these organic molecules from the effects of the sun and weather. The oils migrate to the surface and are released over time into the air. As a result, the composition of the present invention is long lasting and has an improved result over any existing compositions.

Moreover, the pet repellant tire dressing of the present invention is stable over time without any added preservative. The composition of the present invention has a shelf life of over one year. It is known that organic compounds such as citronella oil, cinnamon oil, and piper nigrum oil tend to degrade and lose strength over time due to evaporation and other causes. It is unexpected that the pet repellant tire dressing of the present invention is stable for a year or more.

The citronella oil, cinnamon oil, and piper nigrum oil have pet repellent qualities. In one embodiment, the pet repellent tire dressing of the present invention comprises citronella oil in an amount between 0.10% to 4.0% by weight, cinnamon oil in an amount between 0.04% to 1.6% of the solution by weight, piper nigrum oil in an amount between 0.01% to 0.40%, by weight, a solvent and silicone. In another embodiment, the pet repellent tire dressing includes a commercially available, compatible dye, such as Pylaklor Oil, Bright Blue, LX-6258 or its equivalent. The dye comprises up to 0.2% by weight of the pet repellent tire dressing.

Any commercially available, compatible solvent is used as a component of the present invention. In some embodiments, the solvent is water. In other embodiments, the solvent is a petroleum based solvent. For example, the solvent is an aliphatic hydrocarbon with a carbon chain length greater than n equals 6 (no shorter than hexane), any commercially available mineral spirits, or mineral spirits with a high aliphatic content. The amount of solvent can be used to alter the viscosity of the solution. In embodiments where the pet repellent tire dressing is sprayed on, the level of solvent required is higher. For example, the amount of silicone ranges between 8% and 30% by weight and the amount of solvent ranges between 70% and 92% by weight. In embodiments where the pet repellent tire dressing is applied by spreading or painting with a rag or brush, the amount of solvent needed is lower. For example, the amount of silicone ranges between 16% and 32% by weight and the amount of solvent ranges between 68% and 84% by weight.

Any commercially available silicone can be used as a component of the pet repellent tire dressing of the present invention. In some embodiments, petroleum or water based silicones with viscosities ranging between 100 centipoise and 10,000 centipoise are used. In another embodiment, a blend of petroleum or water based silicone with an average viscosity of between 800 centipoise to 5000 centipoise is used.

The citronella, cinnamon, and piper nigrum oil are dispersed in the silicone and solvent. After the mixture is applied to the tire, the solvent evaporates quickly. The oils remain dispersed in the silicone and are slowly released overtime as they travel to the surface of the silicone solution. The slow release of the oils produces a long lasting, pet repellent effect. This is an improvement over existing pet repellant products which evaporate quickly.

In one embodiment the pet repellent tire dressing contains 0.18% by weight citronella oil, 0.07% by weight cinnamon oil, and 0.02% by weight piper nigrum oil dispersed in a water based silicone with an aqueous solvent. Several tests were performed to determine the effectiveness of this formulation. Each test showed that the present invention has long-lasting, pet deterrent properties. In each test, when the pet deterrent tire dressing was applied to surfaces, it effectively stopped dogs from urinating on those surfaces.

For example, the pet deterrent tire dressing was applied to a wooden telephone pole which a dominant male dog has habitually urinated on for years. The dog stopped urinating on the pole for a period of three weeks after the pet deterrent tire dressing was applied. Several heavy rains occurred during this test, but the dog did not resume urinating on the pole following the rain. In another test, the pet deterrent tire dressing was applied to vehicle tires. The vehicle was driven 25 miles at speeds up to 70 miles per hour. When the vehicle was parked in its normal location at the end of the trip, the owner's male dog did not urinate on the vehicle tires as was its habit. In another test, vehicle wheels were treated with the present invention and the vehicle was left in the presence of eight dogs. None of the dogs urinated on the vehicle tires for at least one week (the duration of the test period). In each of these tests where the tire dressing was applied to vehicle tires, the pet repellent tire dressing of the present invention gave the vehicle tires a pleasing, like-new appearance.

In an alternative embodiment the pet repellent tire dressing contains 0.18% by weight citronella oil, 0.07% by weight cinnamon oil, and 0.02% by weight piper nigrum oil dispersed in a petroleum based silicone with an oil based solvent.

A solution of silicone and solvent with percentages of citronella oil less than 0.1% by weight, cinnamon oil less than 0.04% by weight, and piper nigrum oil less than 0.01% by weight had no pet deterrent effect when tested. When percentages of citronella oil greater than 4% by weight, cinnamon oil greater than 1.6% by weight, and piper nigrum oil greater than 0.4% by weight were added to silicone and solvent, the mixture would cause the animals to sneeze and cough during the test.

Those of skill in the art will recognize that there are many ways to produce the compositions of the present invention. In one embodiment, silicon is added to the solvent (in the given percentages, by weight) in a large, stainless steel vessel attached to an industrial mixer. The silicon and solvent solution is mixed on a slow mix cycle until clarity is achieved. It is important to mix the silicon and solvent until a clear solution is formed in order to minimize the amount of foam generated when the oils are mixed in to the solution. This step takes several minutes. Next, the citronella oil, cinnamon oil, and piper nigrum oil are added (in the given percentages, by weight) in any order and are mixed at a slow agitation rate so as not to produce foam for approximately two (2) hours, or until thoroughly mixed.

The pet repellent tire dressing of the present invention is natural, non-toxic and has no harmful effect on the tire and wheel parts. Portions of a tire and wheel parts were submerged in the solution for six months and no adverse effects were observed.

Other features of the invention will become apparent in the course of the following example which is given for illustration of the invention and are not intended to be limiting thereof.

Example 1

The following is an example of a pet repellent tire dressing formula of the present invention:

| Item | Percentage by Weight |
| --- | --- |
| Low Reactive 1000 cps silicone | 16% |
| Aliphatic Distillate | 83.73% |
| Citronella Oil | 0.18% |
| Cinnamon Oil | 0.07% |
| Piper Nigrum Oil | 0.02% |

Thus, it is seen that the pet repellant tire dressing of the present invention readily achieves the ends and advantages mentioned as well as those inherent therein. While certain preferred embodiments of the invention have been illustrated and described for the purposes of the present disclosure, numerous changes in the arrangement and construction of parts may be made by those skilled in the art, which changes are encompassed within the scope and spirit of the present invention as defined by the following claims.

What is claimed is:

1. A pet repellent tire dressing comprising:
citronella oil in an amount ranging from about 0.10% to 4.0% by weight;
cinnamon oil in an amount ranging from about 0.04% to 1.6% by weight;
piper nigrum oil in an amount ranging from about 0.01% to 0.40% by weight;
silicone in an amount ranging from about 8% to 30% by weight; and
the remainder a solvent.

2. The pet repellent tire dressing of claim 1 where:
the silicone is a water based silicone.

3. The pet repellent tire dressing of claim 1 where:
the silicone is a petroleum based silicone.

4. The pet repellent tire dressing of claim 1 where:
the solvent is water.

5. The pet repellent tire dressing of claim 1 where:
the solvent is aliphatic distillate.

6. The pet repellent tire dressing of claim 1 further comprising:
a dye in an amount up to 0.02% by weight.

7. The pet repellent tire dressing of claim 1 wherein:
the citronella oil comprises about 0.18% by weight.

8. The pet repellent tire dressing of claim 1 wherein:
the cinnamon oil comprises about 0.07% by weight.

9. The pet repellent tire dressing of claim 1 wherein:
the piper nigrum oil comprises about 0.02% by weight.

10. A pet repellent tire dressing comprising:
citronella oil in an amount of about 0.18% by weight;
cinnamon oil in an amount of about 0.07% by weight;
piper nigrum oil in an amount of about 0.02% by weight;
silicone in an amount of about 16% by weight; and
the remainder a solvent.

11. The pet repellent tire dressing of claim 10 further comprising:
a dye in an amount up to 0.02% by weight.

12. The pet repellent tire dressing of claim 10 where:
the silicone is a water based silicone.

13. The pet repellent tire dressing of claim 10 where:
the silicone is a petroleum based silicone.

14. The pet repellent tire dressing of claim 10 where:
the solvent is water.

15. The pet repellent tire dressing of claim 10 where:
the solvent is aliphatic distillate.

16. A pet repellent tire dressing comprising:
citronella oil in an amount ranging from about 0.10% to 4.0% by weight;
cinnamon oil in an amount ranging from about 0.04% to 1.6% by weight;
piper nigrum oil in an amount ranging from about 0.01% to 0.40% by weight;
silicone in an amount ranging from about 16% to 32% by weight; and
the remainder a solvent.

17. The pet repellent tire dressing of claim 16 further comprising:
a dye in an amount up to 0.02% by weight.

18. The pet repellent tire dressing of claim 16 where:
the silicone is a water based silicone.

19. The pet repellent tire dressing of claim 16 where:
the silicone is a petroleum based silicone.

20. The pet repellent tire dressing of claim 16 wherein:
the solvent is selected from the group consisting of water and aliphatic distillate.

\* \* \* \* \*